US012708261B2

(12) United States Patent
Boutinon et al.

(10) Patent No.: US 12,708,261 B2
(45) Date of Patent: Aug. 18, 2026

(54) METHOD AND SYSTEM FOR EVALUATING VISUAL ACUITY OF A PERSON

(71) Applicant: Essilor International, Charenton-le-pont (FR)

(72) Inventors: Stéphane Boutinon, Charenton-le-pont (FR); Marius Peloux, Charenton-le-pont (FR); Marion Swital, Charenton-le-pont (FR); Philippe Pinault, Charenton-le-pont (FR); Marie-Virginie Berbet, Charenton-le-pont (FR)

(73) Assignee: Essilor International, Charenton-le-Pont (FR)

(*) Notice: Subject to any disclaimer, the term of this patent is extended or adjusted under 35 U.S.C. 154(b) by 668 days.

(21) Appl. No.: 18/005,271

(22) PCT Filed: Jul. 15, 2021

(86) PCT No.: PCT/EP2021/069909

§ 371 (c)(1),
(2) Date: Jan. 12, 2023

(87) PCT Pub. No.: WO2022/013410

PCT Pub. Date: Jan. 20, 2022

(65) Prior Publication Data

US 2023/0255474 A1 Aug. 17, 2023

(30) Foreign Application Priority Data

Jul. 15, 2020 (EP) .................................... 20315350

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0033* (2013.01); *A61B 3/005* (2013.01); *G06T 3/40* (2013.01);
(Continued)

(58) Field of Classification Search
CPC ....... A61B 3/032; A61B 3/0033; A61B 3/005; A61B 2090/061; A61B 3/028; A61B 3/02; G06T 3/40; G06T 7/50; G06T 2207/30004
See application file for complete search history.

(56) References Cited

U.S. PATENT DOCUMENTS 977,065 A 11/1910 Berry
9,532,709 B2 1/2017 Carrafa et al.
(Continued)

FOREIGN PATENT DOCUMENTS

CN 108478185 A 9/2018
EP 3 295 862 A1 3/2018
(Continued)

OTHER PUBLICATIONS

International Search Report issued Feb. 2, 2022 in PCT/EP2021/069909 filed on Jul. 15, 2021, 15 pages.
(Continued)

*Primary Examiner* — Jeffrey G. Hoekstra
(74) *Attorney, Agent, or Firm* — Oblon, McClelland, Maier & Neustadt, L.L.P.

(57) ABSTRACT

A method for evaluating the visual acuity of a person using a mobile device having at least a front camera and a screen, the method including a user positioning step during which the user of a mobile device positions himself in front of a mirror at a predefined distance d/2, a mobile device positioning step during which the mobile device is positioned with the front camera of the mobile device facing the mirror,
(Continued)

a distance measuring step during which a distance d between the front camera of the mobile device and a virtual image of the mobile device in the mirror is measured, a displaying step during which the screen of the mobile device displays optotypes, and an evaluation step during which the visual acuity of the user is evaluated.

9 Claims, 4 Drawing Sheets

(51) Int. Cl.
*A61B 90/00* (2016.01)
*G06T 3/40* (2024.01)
*G06T 7/50* (2017.01)

(52) U.S. Cl.
CPC .......... *G06T 7/50* (2017.01); *A61B 2090/061* (2016.02); *G06T 2207/30004* (2013.01)

(56) References Cited

U.S. PATENT DOCUMENTS

| | | | |
|---|---|---|---|
| 9,770,165 | B2 | 9/2017 | Carrafa |
| 2012/0050685 | A1 | 3/2012 | Bartlett et al. |
| 2014/0354949 | A1 | 12/2014 | Bakar et al. |
| 2016/0120402 | A1 | 5/2016 | Limon |
| 2017/0079523 | A1 | 3/2017 | Limon |
| 2017/0164822 | A1 | 6/2017 | Kalder et al. |
| 2018/0296084 | A1 | 10/2018 | Kawahara et al. |
| 2019/0231185 | A1 | 8/2019 | Allione et al. |
| 2019/0307324 | A1 | 10/2019 | Limon |
| 2020/0069172 | A1 | 3/2020 | Perrin et al. |
| 2020/0253471 | A1 | 8/2020 | Prevoo et al. |
| 2021/0007599 | A1 | 1/2021 | Grondin et al. |

FOREIGN PATENT DOCUMENTS

| | | | |
|---|---|---|---|
| EP | 3 542 704 | A1 | 9/2019 |
| JP | 2015-57167 | A | 3/2015 |
| JP | 2018-500957 | A | 1/2018 |
| RU | 2 210 972 | C1 | 8/2003 |
| WO | WO 2010/132305 | A1 | 11/2010 |
| WO | WO 2014/195951 | A1 | 12/2014 |
| WO | WO 2016/083094 | A1 | 6/2016 |
| WO | WO 2019/017785 | A1 | 1/2019 |

OTHER PUBLICATIONS

Japanese Office Action issued Dec. 9, 2024, in corresponding Japanese Patent Application No. 2023-502809 (with English Translation), 13 pages.

Korean Office Action issued Dec. 17, 2024, in corresponding Korean Patent Application No. 10-2023-7001181 (with English Translation), 18 pages.

Japanese Office Action issued Jul. 1, 2025 in Japanese Patent Application No. 2023-502809 with English translation, 13 pgs.

METHOD AND SYSTEM FOR EVALUATING VISUAL ACUITY OF A PERSON

TECHNICAL FIELD

The disclosure relates to the evaluation of the visual acuity of a person. In particular, the disclosure relates to a method for evaluating the visual acuity of a person using a mobile device. The disclosure further relates to a mobile device for measuring the visual acuity of a person.

Furthermore, the disclosure relates to a display system for use to determine the visual acuity of a person.

BACKGROUND

Usually, the naked eye visual acuity or corrected visual acuity of a person is evaluated by eye-care professionals. As such, it requires setting up an appointment with an ophthalmologist which makes it difficult to regularly and frequently check its visual acuity.

Methods of the prior have tried to develop solutions for checking visual acuity without requiring the intervention of an eye-care professional.

However, these methods usually require the use of a laptop which makes it less accessible to a part of the population. Moreover, most of the methods of the prior art require a calibration procedure, for example using a credit card or shoe size, to determine and set up the distance between the laptop and the user prior to the procedure for measuring visual acuity. As such the distance is not properly controlled during the procedure which can lead to errors of measurements of the visual acuity.

Some methods of the prior art propose self-measurement solutions, for example using a smartphone application. However, the measurement is performed at arm's length while the user hand-held the smartphone which limit the evaluation of the visual acuity to near vision. Other smartphone applications, generally proposed for professional use, allows measuring visual acuity of a person in far vision but require the intervention of a second person, generally the eye care professional.

Therefore, there is a need for a solution to, simply, quickly, and accurately, evaluate the visual acuity of a person.

SUMMARY

To this end, the disclosure proposes a method for evaluating the visual acuity of a person using a mobile device comprising at least a front camera and a screen, the method comprising:

- a user positioning step during which the user of a mobile device positions himself in front of a mirror at a predefined distance d/2;
- a mobile device positioning step during which the mobile device is positioned with the front camera of the mobile device facing the mirror;
- a distance measuring step during which a distance d between the front camera of the mobile device and a virtual image of the mobile device in the mirror is measured;
- a displaying step during which the screen of the mobile device displays optotypes; and
- an evaluation step during which the visual acuity of the user is evaluated.

Advantageously, the method according to the disclosure allows to evaluate the visual acuity of a person easily and accurately.

Advantageously, the evaluation according to the method can be performed at home by the user. An optometrist at a remote location can then check if the test is precisely done.

The user is no longer needed to go to an eyecare professional center to perform visual acuity evaluation test. This is more convenient for the user which has no more transportation or time constraints to perform the evaluation.

According to further embodiments which can be considered alone or in combination:

- during the mobile device positioning step, the mobile device is positioned vertically over an eye of the user; and/or
- during the evaluation step, the binocular visual acuity of the user is measured and/or
- during the evaluation step, the monocular visual acuity of the user is measured and/or
- the method further comprises prior to the displaying step, a distance controlling step during which the measured distance d is compared to the predefined distance d/2; and/or
- the method further comprises a notification step during which a notification is sent to the user based on the comparison of the measured distance d and the predefined distance d/2; and/or
- the notification indicates that the person is too close to the mirror when the measured distance d is smaller than or equal to $2\times(d/2)-\Delta1$; and/or
- the notification indicates that the person is too far to the mirror when the measured distance d is greater than or equal to $2\times(d/2)+\Delta2$; and/or
- the size of the optotypes displayed during the displaying step is adapted based on the measured distance d; and/or
- the angular size of the optotypes displayed during the displaying step is adapted based on the measured distance d; and/or
- the distance d/2 between the front camera and the mirror is regularly measured during the displaying and the evaluation steps, and the size and/or angular size of the optotypes displayed during the displaying step is adapted in real-time based on the measured distance d/2; and/or
- the method further comprises a mobile device data receiving step during which mobile device data are received, the mobile device data comprising at least screen data relating at least to the physical size of the screen of the mobile device and camera data relating at least to the angular resolution of the front camera's pixel, and the distance d is measured based at least on the mobile device data; and/or
- the method further comprises a camera data receiving step during which the front camera of the mobile device obtains data of the scene, and the distance d is measured based at least on the camera data; and/or
- the predefined distance d/2 is greater than or equal to 1.5 m, preferably greater than or equal to 2.0 m and the visual acuity is evaluated for far vision condition; and/or
- the predefined distance d/2 is smaller than or equal to 0.5 m, preferably smaller than or equal to 0.25 m and the visual acuity is evaluated for near vision condition; and/or
- the method further comprises an input receiving step during which indication is received from the user in response to the displayed optotype, and the visual acuity of the user is evaluated based on the received indication from the user; and/or the optotypes displayed on the screen of the mobile device during the displaying step comprises a single Landolt-C with varying directions/orientation, and the indication received from the user relates to a direction/orientation of an aperture of the Landolt-C perceived by the user; and/or the perceived direction of the Landolt-C aperture is indicated by the user using speech recognition and/or gesture recognition and/or movement of the mobile device; and/or the displayed optotype further comprises a movable cursor and the perceived direction of the Landolt-C on the screen of the mobile device is indicated by a position of the movable cursor; and/or the mobile device comprises physical plus and minus volume buttons, and wherein the movable cursor is controlled by the person using the physical plus and minus volume buttons of the mobile device; and/or the mobile device can be hold with a single hand, for example a smartphone, a phablet, or a tablet.

The disclosure further relates to a computer-readable storage medium having a program recorded thereon, wherein the program makes the computer execute a method according to the disclosure.

The disclosure also relates to a non-transitory program storage device, readable by a computer, tangibly embodying a program of instructions executable by the computer to perform a method comprising:

measuring a distance d between a front camera of a mobile device and a mirror facing the front camera of the mobile device;

displaying optotypes on a screen of the mobile device;

receiving inputs from a user of the mobile device, and evaluating a visual acuity of the user based on the received inputs.

The disclosure further relates to mobile device comprising a screen;

at least one front camera;

a memory configured to store sequences of instructions; and a processor coupled to the memory, the screen and the at least one camera, wherein the processor is configured to execute the sequences of instructions to:

measure a distance d between the front camera and a mirror facing the front camera;

display on the screen of the mobile device optotypes;

receive inputs from a user of the mobile device; and evaluate a visual acuity of the user based on the received inputs.

Furthermore, the disclosure relates to display system for use to determine the visual acuity of a person, the display system comprising:

controlling means for identifying and processing input data, the input data being received from the person;

displaying means for displaying at least one optotype and at least one movable cursor, the optotype being oriented in a direction selected from a list of predefined orientation, and the movable cursor being configured to be displayed in any of the directions of the list of predefined directions, the orientation of the movable cursor displayed being based on the inputs processed by the controlling means.

Advantageously, the display system provides a simple and accessible way to implement the method for evaluating a visual acuity of a person.

The mobile device system may comprise the display system. The displaying means may be formed by the screen of the mobile device. The mobile device may further comprise the controlling means of the display system, said controlling means being configured for identifying and processing input data, the input data being received from the person.

BRIEF DESCRIPTION OF THE DRAWINGS

Embodiments of the invention will now be described, by way of example only, and with reference to the following drawings in which.

Elements in the figures are illustrated for simplicity and clarity and have not necessarily been drawn to scale. For example, the dimensions of some of the elements in the figure may be exaggerated relative to other elements to help to improve the understanding of the embodiments of the present invention.

DETAILED DESCRIPTION

The disclosure relates to a method for evaluating the visual acuity of a person using a mobile device 2. Visual acuity commonly refers to the clarity of vision, but technically rates a person's ability to recognize small details with precision. The visual acuity may be evaluated for a user with or without his glasses.

In the sense of the invention, a mobile device is a portable computer device that can be used independently, and small enough to be easily carried by the user and operated in the hand. For example, the mobile device may be a smartphone, a phablet, or a tablet.

For the sake of clarity and simplicity, the mobile device will be exemplified using a smartphone in the following disclosure. However, a person of ordinary skill in the art would be able to easily adapt the following examples to any other mobile device as defined by the present disclosure.

Figure 4:
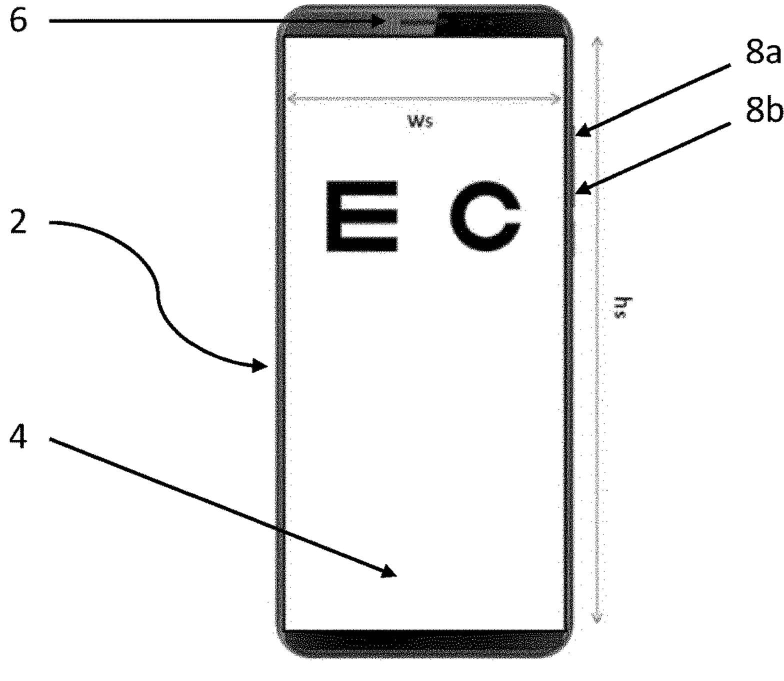
FIG. 4 illustrates an example of mobile device according to an embodiment of the disclosure.

As illustrated in FIG. 4, the mobile device 2 comprises at least a screen 4 and a front camera 6. The screen 4 and the front camera 6 are positioned on the same face of the mobile device 2.

The mobile device 2 further comprises a memory 8 configured to store sequences of instructions and a processor 12 coupled to the memory 10 and configured to execute the sequences of instructions stored in the memory 10.

Figure 1:
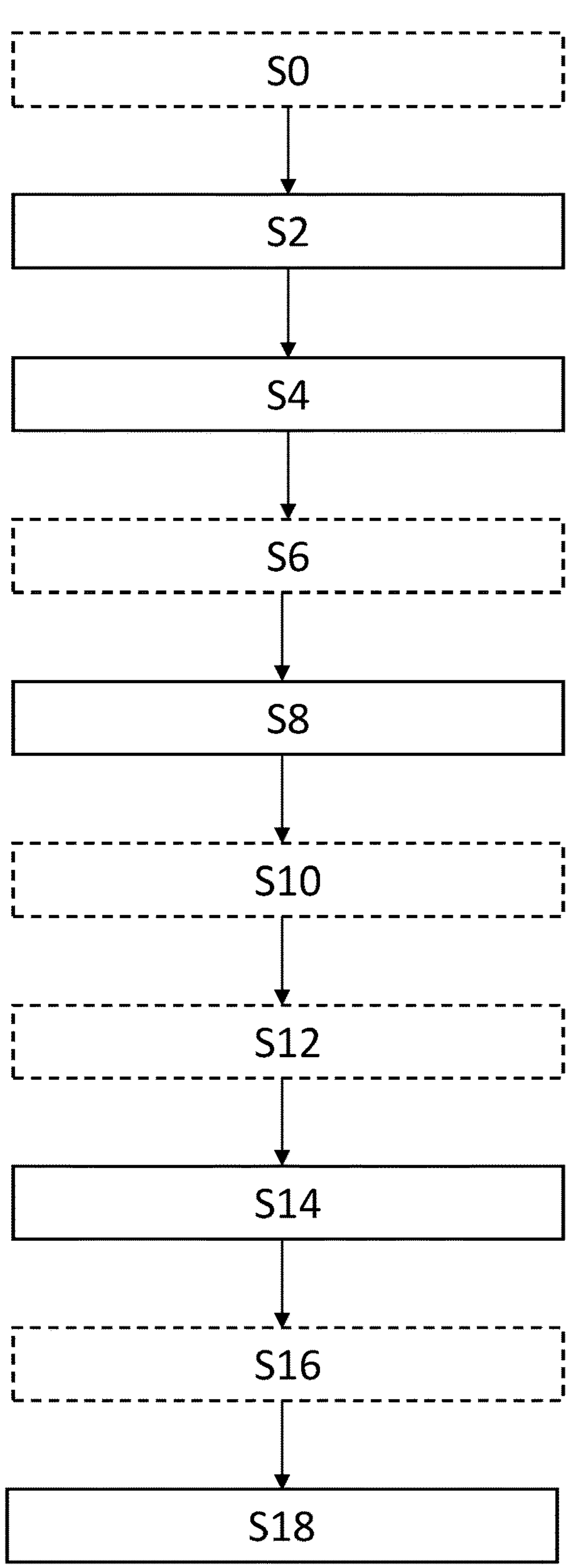
FIG. 1 illustrates a chart-flow embodiment of the method for evaluating the visual acuity of a person using a mobile device.

As illustrated in FIG. 1, the method for evaluating the visual acuity of a person comprises a user positioning step S2. During the user positioning step S2, the user of the mobile device positions himself in front of a mirror at a predefined distance d/2 from the mirror.

Figure 2:
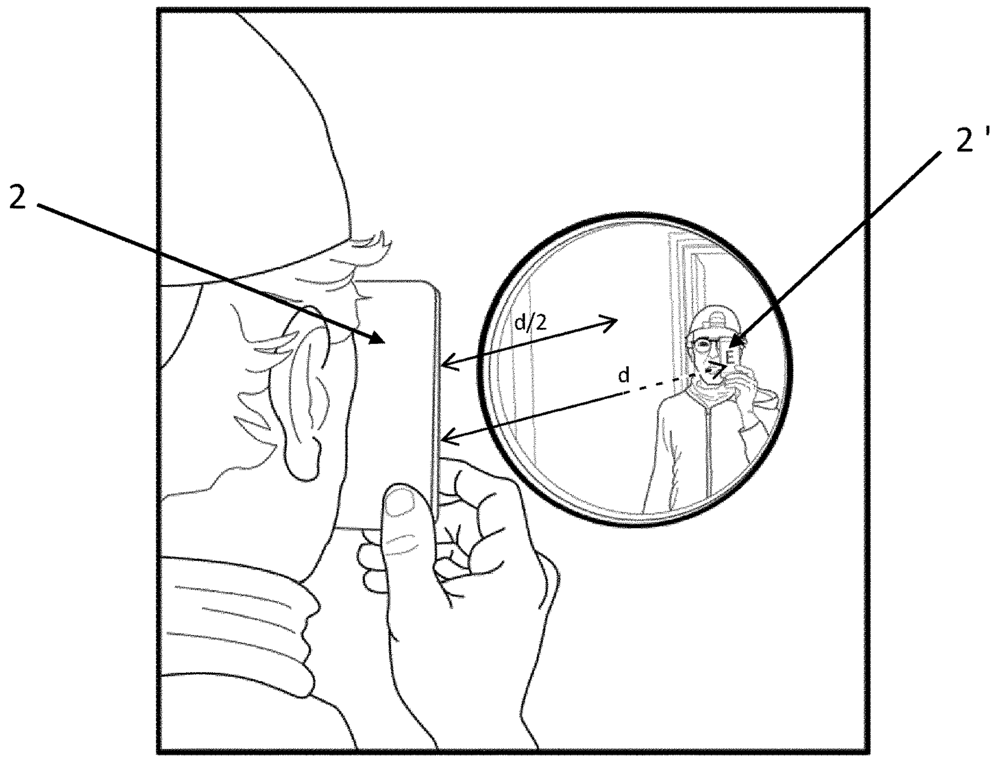
FIG. 2 illustrates a person measuring his visual acuity according to an embodiment of the disclosure.
Figure 3A:
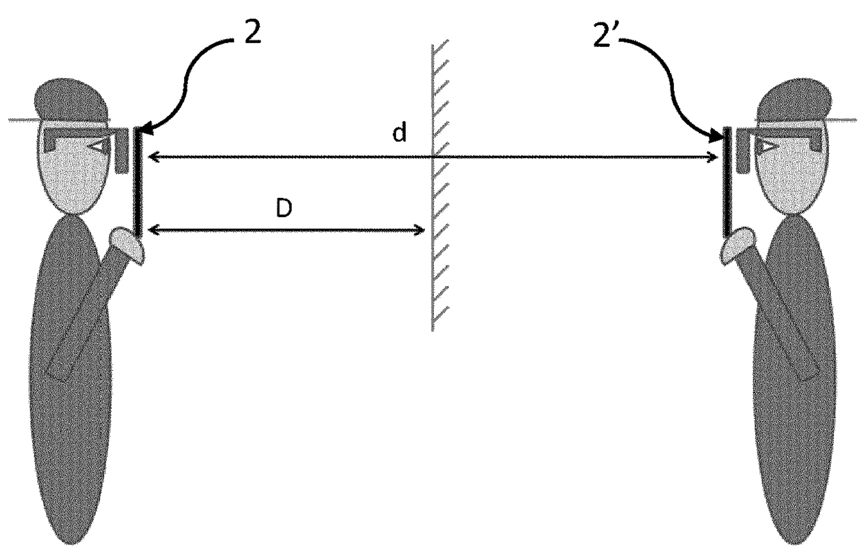
FIGS. 3*a* and 3*b* illustrate a person measuring his visual acuity according to an embodiment of the disclosure

As illustrated in FIGS. 2 and 3, the user is positioned at a predefined distance d/2 facing the mirror 20 to see the virtual images created by the light reflected on the surface of the mirror. Preferably, the mirror 20 is a plane mirror. When the user is positioned at the predefined distance d/2, the distance between said user and the virtual image he sees in the mirror may be defined as equal to two times the predefined distance d/2.

According to an embodiment of the invention, the predefined distance d/2 is greater than or equal to 1.5 m, preferably greater than or equal to 2.0 m. Advantageously, the predefined distance d/2 is greater than or equal to 2.5 m to better relax accommodation. With such conditions, the method of the disclosure evaluates the visual acuity of the user for far vision.

Alternatively, the predefined distance d/2 may be smaller than or equal to 0.5 m, preferably greater than or equal to 0.25 m. With such conditions, the method of the disclosure evaluates the visual acuity of the user for near vision.

As illustrated in FIG. 1, the method for evaluating the visual acuity of a person further comprises a mobile device positioning step S4. During the mobile device positioning step S4, the user positions the mobile device 2 to have the front camera 6 facing the mirror.

As illustrated in FIGS. 2 and 3, the user positions the mobile device 2 with the front camera 6 facing the mirror 20. Preferably, the mobile device 2 is positioned vertically to be substantially parallel to the plane of the mirror 20. More preferably, the mobile device 2 is positioned as close as possible to the head of the user.

According to an embodiment of the disclosure, the mobile device 2 is positioned vertically over one eye of the user and the visual acuity of the other eye is evaluated. Advantageously, having the mobile device covering the eye of the user allow to facilitate evaluating the monocular visual acuity of the non-covered eye of the user.

As illustrated in FIG. 1, the method for evaluating the visual acuity of a person further comprises a distance measuring step S8. During the distance measuring step S8, the distance d between the front camera of the mobile device and a virtual image of the mobile device is measured.

The distance d between the front camera of the mobile device 2 and the virtual image 2' created by the mirror 20 on which said mobile device is reflected may be measured using the mobile device 2 itself.

According to an embodiment of the disclosure illustrated in FIG. 1, the method for evaluating the visual acuity of a person may comprise a mobile device data receiving step S0 during which mobile device data are received. The mobile device data comprise at least screen data relating at least to the physical size of the screen of the mobile device and at least camera data relating at least to the angular resolution of the front camera's pixel.

The screen data enables to adapt the display of optotypes and more particularly, the positioning and dimension of the optotypes based on the physical size of screen of the mobile device.

The screen data enables to determine a size of an element to be displayed, having a known dimension, during the distance measuring step S8.

In an embodiment, the element displayed during the distance measuring step is an optotype.

As illustrated on FIG. 4, screen's physical size expressed as $w_s \times h_s$, with $w_s$ the physical screen's width and $h_s$ the physical screen's height, can be obtained from any mobile device 2 based on the resolution of the screen $m_s \times n_s$ and the pixel density of the screen $D_{p,s}$ (expressed in dots per inches or dpi). The resolution and the pixel density of the screen can be easily obtained from the mobile device's operating system (OS) or from manufacturer data.

Knowing the values $m_s$, $n_s$, and $D_{p.s}$, the values of $w_s$ and $h_s$ can be determined using the following equation:

$$\left\{ w_s = \frac{m_s}{D_{p,s}} h_s = \frac{n_s}{D_{p,s}} \right. \quad (1)$$

By way of non-limiting example, the calculation of the screen's physical size of a mobile device 2 is exemplified for a specific smartphone S with a screen resolution $m_s \times n_s$ equal to 1440×3040 and a pixel density $D_{p,s}$ equal to 550 dpi. Using equation (1), we obtain a physical screen's width $w_s$ equal to 66.5 mm and a physical screen's height equal to 140.4 mm.

Alternatively, the physical screen's size can be calculated from the diagonal physical size of the screen and the resolution.

The angular resolution of the front camera's pixel $p_{c,\theta}$ can be obtained from a front camera's pixel size $p_c$ (expressed in meters) and a focal length $f_c$. Similarly, the front camera's pixel size and the focal length can be obtained from the mobile device's operating system (OS) or from manufacturer data.

Knowing the values $p_c$ and $f_c$, the value $p_{c,\theta}$ can be determined using the following equation:

$$p_{c,\theta} = 2a\tan\left(\frac{p_c}{2f_c}\right) \approx \frac{p_c}{f_c} \quad (2)$$

The display of an element, having a known dimension, on the screen of a mobile device having a front camera facing a mirror, enables to estimate the distance d, during the distance measuring step S8, based on the angular resolution of the front camera.

In an embodiment, the element displayed during the distance measuring step is an optotype.

By way of non-limiting example, the calculation of the angular resolution of the front camera's pixel of a mobile device 2 is exemplified for the specific smartphone S with a front camera pixel's size $p_c$ equal to 1.22 μm and a focal length equal to 3.34 mm. Using equation (2), we obtain angular resolution of the front camera's pixel $p_{c,\theta}$ equal to 0.021°.

For simplicity's sake the camera's pixel physical size $p_c$ is considered to have the same value in horizontal and vertical directions. However, the reasoning could be easily extended if this condition is not true. For a better precision, the value $f_c$ can be replaced by the real distance between the lens and the camera's sensor of the mobile device since the specified working distance of the front camera is likely not set at infinity. However, the Inventors have observed that equation (2) leads to enough accuracy. Alternatively, the real distance between the lens and the camera's sensor can be calculated by assuming that the camera is set for a finite distance between 0.5 m and 1.0 m, preferably at 0.8 m.

The distance d between the front camera of the mobile device 2 and the virtual image created by the mirror 20 on which said mobile device is reflected may be measured based on the mobile device data and data received by the front camera 6 of the mobile device 2. Advantageously, the measurement of the distance according to the disclosure does not require a step of calibration.

Advantageously estimating the distance d in the distance measuring step S8, based on mobile device data and the dimension of the element to be displayed on the screen of the mobile device during the distance measuring step S8 enables to avoid requiring a distance calibration step.

It is no longer required a calibration step wherein the element displayed on the screen of the mobile device is firstly displayed at a known distance from a mirror. Alternatively it is no longer needed to use an object (for example a credit card), other than the mobile device to calibrate the screen of the mobile device.

A direct measurement of the distance d between the front camera and the virtual image of the element is performed based one the known size of the element displayed on the screen and the mobile device data.

In an embodiment, the distance d can be continuously estimated during the visual acuity evaluation method, knowing the width of the mobile device screen and adapting the dimension of the displayed optotype based on the mobile device screen width.

In an embodiment, while displaying an optotype on the screen, during the visual acuity evaluation method, the distance d can be continuously estimated, as the dimension of the displayed optotype and the mobile device data are known. For example, the optotype size may be defined based on the width of the screen of the mobile device.

In an embodiment, when intrinsic parameter of the mobile device determining mobile device data are known, the precision and/or robustness of image processing are improved.

Accordingly, the method for evaluating the visual acuity of a person may further comprise a camera data receiving step S6 during which the front camera 6 of the mobile device 2 obtains data related to the scene it is facing. Typically, the front camera 6 of the mobile device 2 captures images and/or videos of the scene, and particularly of the mirror and of the virtual image formed by the mirror facing the front camera. The images and/or videos may further be processed to extract data relating to the size of the virtual image of the screen of the mobile device reflected by the mirror. For example, the width of the screen of the virtual mobile device reflected by the mirror may be expressed as a number of pixels $m_{c,d}$ on a picture/video recorded by the front camera. Similarly, the height of the screen of the virtual mobile device reflected by the mirror may be expressed as a number of pixels $n_{c,d}$ on a picture/video recorded by the front camera.

The distance d between the front camera of the mobile device 2 and the virtual image created by the mirror 20 can be determined using the following equations:

$$m_{c,d} \times p_{c,\theta} = a\tan\left(\frac{w_s}{d}\right) \approx \frac{w_s}{d}, \tag{3}$$

And then:

$$d \approx \frac{w_s}{m_{c,d} \times p_{c,\theta}} \tag{4}$$

Alternatively, the distance d may be measured by displaying on the screen 4 of the mobile device 2, different shapes of predefined known dimensions. Knowing the dimension of the displayed shapes, the distance d can be measured using equations (2) to (4).

The method for evaluating the visual acuity of a person may further comprise a parallelism measuring step during which the parallelism of the mobile device 2 in relation to the mirror 20 is measured. When the mirror is vertical, the parallelism of the mobile device may be measured using the IMU of the mobile device. Alternatively, the parallelism of the mobile device 2 may be measured by displaying on the screen 4 of the mobile device 2, a predefined shape, for example a rectangle and comparing the displayed shape with the shape of the virtual image created by the mirror 20. For example, when the mobile device 2 is not parallel to the mirror 20, a rectangle displayed on the screen and reflected by the mirror 20 will generates a trapezoidal shape.

As illustrated in FIG. 1, the method for evaluating the visual acuity of a person may further comprise a distance controlling step S10. During the distance controlling step, the measured distance d between the front camera of the mobile device 2 and the virtual image created by the mirror 20 is compared to the predefined distance d/2.

Similarly, the method for evaluating the visual acuity of a person may further comprise a parallelism controlling step during which the shape of the virtual image generated by the mirror 20 is compared to a predefined shape displayed by the screen 4.

The method for evaluating the visual acuity of a person may further comprise a notification step S12. During the notification step, a notification is sent to the user based on the comparison of the measured distance d and the predefined distance d/2.

For example, when the measured distance d between the front camera of the mobile device 2 and the virtual image created by the mirror 20 is smaller than two times the predefined distance d/2, the notification may indicate that the user is too close to the mirror. Additionally, a deviation Δ1 may be considered. The deviation Δ1 represents a tolerance value of the predefined distance d/2. When the measured distance d is smaller than (2×(d/2)−Δ1), the notification may indicate that the user is too close to the mirror. For example, the deviation Δ1 may correspond to a variation of 20%, preferably 10% of the predefined distance d/2.

For example, when the measured distance d between the front camera of the mobile device 2 and the virtual image created by the mirror 20 is greater than two times the predefined distance d/2, the notification may indicate that the user is too far to the mirror. Additionally, a deviation Δ2 may be considered. The deviation Δ2 represents a tolerance value of the predefined distance d/2. When the measured distance d is smaller than (2×(d/2)+Δ2), the notification may indicate that the user is too close to the mirror. For example, the deviation Δ2 may correspond to a variation of 20%, preferably 10% of the predefined distance d/2.

Alternatively, a maximal deviation ΔD from the value of the predefined distance d/2 may be defined. When the measured distance d is smaller than (2×(d/2)−ΔD), the notification may indicate that the user is too close to the mirror. Similarly, when the measured distance d is greater than (2×(d/2)+ΔD), the notification may indicate that the user is too far from the mirror. The maximal deviation ΔD may correspond to a variation of 20%, preferably 10% of the predefined distance d/2.

Additionally, during the notification step S12, a notification may be sent to the user based on the comparison of the shape of the virtual image generated by the mirror 20 and a predefined shape displayed by the screen 4. For example, when the variation between the compared shapes is too important, for example a variation of 10%, the notification may indicate that the mobile device 2 is not parallel to the mirror 20.

As illustrated in FIG. 1, the method for evaluating the visual acuity of a person further comprises a displaying step S14. Preferably, the displaying step is performed after the distance controlling step and the notification step. During the displaying step, optotypes are displayed on the screen 4 of the mobile device 2. In the sense of the disclosure, optotypes refer to standardized symbols commonly used to test the vision of a person.

Figure 3B:
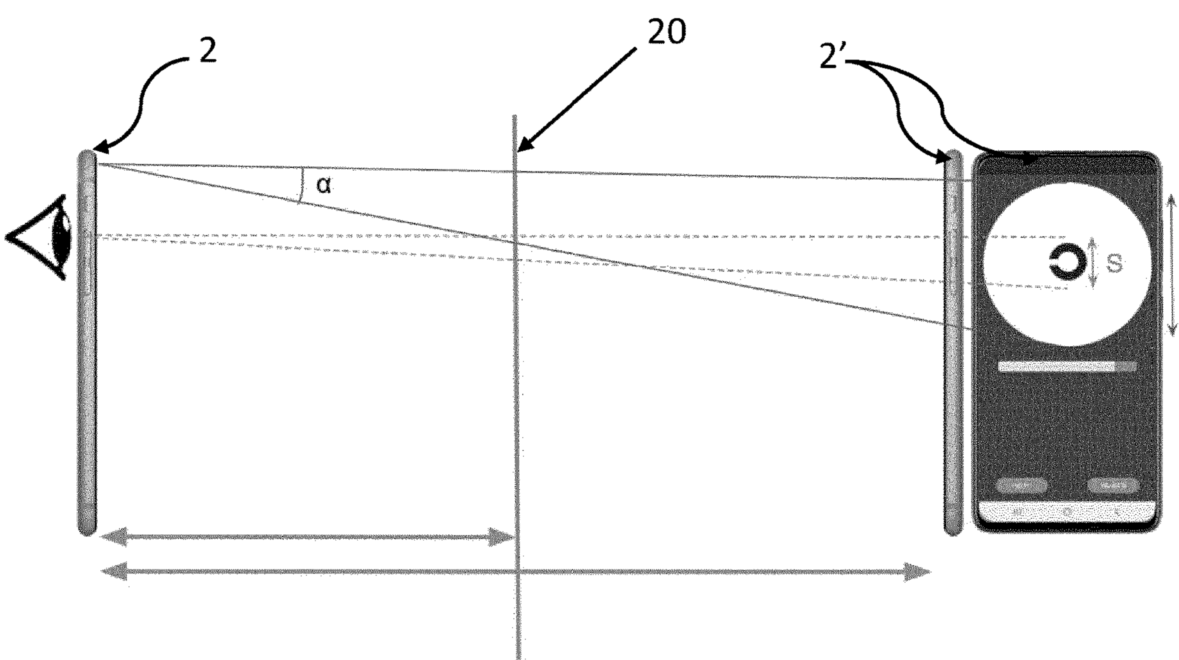

As illustrated in FIGS. 2 and 3*b*, the optotypes displayed on the screen 4 of the mobile 2 are reflected on the mirror which generates virtual images of the optotypes. Preferably, a symmetry is applied to the displayed optotype. Advantageously, the user will perceive the virtual images of the displayed optotypes with the correct orientation.

The displayed optotypes may be Landolt C or Snellen E or any other standardized optotypes, letters, or drawings. The optotypes may be displayed one by one on the screen 4 of the mobile device during the displaying step. Alternatively, optotypes may be displayed line by line with multiple optotype on each line. The size and/or orientation and/or contrast of each optotype may vary during the displaying step. Alternatively, multiple lines of optotypes may be displayed at the same time, with optotypes of different size and/or orientation and/or contrast on each line, for example ETDRS charts like or 2-lines VR800 procedures. Alternatively, the displayed optotypes may correspond to words or short sentences.

During the displaying step, the size of the displayed optotypes may be adapted based on the measured distance d. Alternatively, the size of the displayed optotypes may be determined based on the predefined distance d/2 from the mirror.

Similarly, the angular size of the displayed optotypes on the screen 4 of the mobile device 2 may be adapted based on the measured distance d.

By way of non-limiting example, the optotype considered for the following calculation is a Landolt ring with an aperture so that the virtual image at a distance d of the displayed Landolt ring has an angular size of $\Delta\theta$. The physical size $\Delta s$ of the aperture displayed on the screen is given by the following equation:

$$\Delta s = d \times \tan(\Delta\theta) \quad (5)$$

For example, for a measured distance of 4.0 m, the aperture of the displayed Landolt ring M for a visual acuity of 10/10 should be equal to 1'. Using equation (5) physical size $\Delta s$ of the aperture displayed on the screen is approximatively equal to 1.16 mm. For a mobile device 2 corresponding to the specific smartphone S, a physical size $\Delta s$ of the aperture displayed on the screen equal to 1.16 mm corresponds to a number of pixel ($\Delta s/p_s$) approximately equal to 25 pixels on the screen.

According to an embodiment of the disclosure, the distance d between the front camera and the mirror is frequently measured during the displaying step. For example, the distance d may be measured before displaying a different optotype or series of optotypes. Preferably, the distance d between the front camera and the mirror is measured in real time.

Advantageously, it allows updating regularly, for example in real time, the size and/or the angular size of the displayed optotypes on the screen of the mobile device, thereby providing a more accurate evaluation of the visual acuity of the person.

As illustrated in FIG. 1, the method for evaluating the visual acuity of a person further comprises an evaluation step S18. During the evaluation step, the visual acuity of the user is evaluated.

The method for evaluating the visual acuity of a person may further comprise, prior to the evaluation step, an input receiving step S16. During the input receiving step, indications are received from the user in response to the displayed optotype. The indication of the user may be received using speech recognition and/or gesture recognition and/or mobile device movement.

When the optotypes displayed on the screen 4 of the mobile device 2 are words or short sentences, the user may identify the letter or read the sentences. These indications received from the user may be obtained using speech recognition, for example through a microphone of the mobile device.

When the optotypes displayed on the screen 4 of the mobile device 2 are Landolt-C with an aperture having different directions, the user may indicate the direction of the aperture he perceived. The indication relating to the direction of the aperture perceived by the user may be obtained by speech recognition using a microphone of the mobile device, mobile device movement using an IMU of the mobile device or the front camera of the mobile device, and head movement and/or arm movement using the front camera of the mobile device.

As illustrated on FIG. 4, the mobile device 2 may further comprise physical plus and minus volume buttons 8*a* and 8*b*. Preferably, the plus volume button 8*a* and the minus volume button 8*b* are disposed on the side of the mobile device 2, for example on the left side of the mobile device 2 when facing the screen. The plus and minus volume buttons 8*a* and 8*b* may be used by the user to provide an indication during the input receiving step S16.

Figure 5:
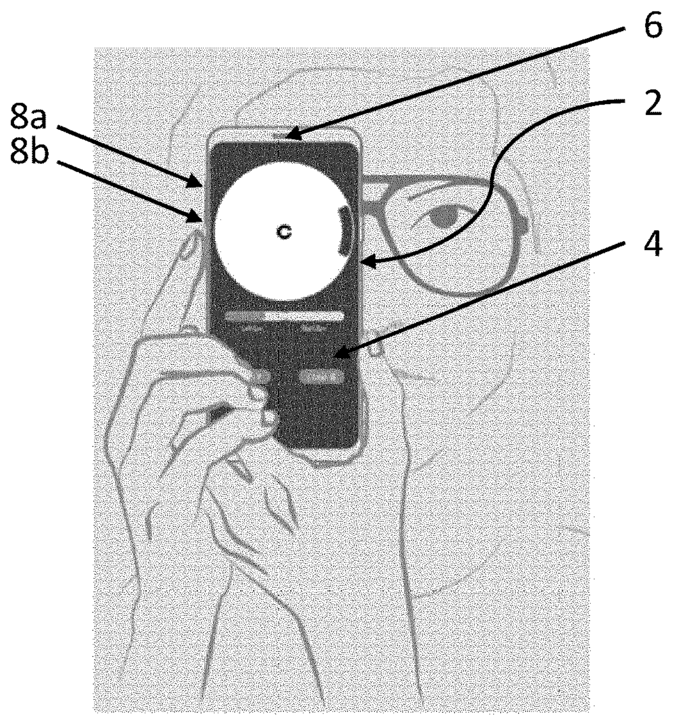
FIG. 5 illustrate a person measuring his visual acuity according to an embodiment of the disclosure.

As illustrated in FIG. 5, the displayed optotypes may be Landolt-C with an aperture having different directions. The displayed optotypes may further comprise a movable cursor 50. The movable cursor may be for example, a circular art that move along the different possible directions of the aperture of the Landolt-C. In such case, the user may utilize the physical plus and minus buttons 8*a* and 8*b* of the mobile device to have the direction of the movable cursor 50 aligned with the perceived aperture of the Landolt-C. The chosen position of the cursor may then be validated after a short waiting period, for example comprised between 0.5 sec and 2.0 sec, preferably after a waiting period of 1.0 sec.

The visual acuity of the user may be evaluated during the evaluation step based on the received indications from the user.

According to an embodiment of the disclosure, during the displaying step, a first series various randomized optotypes, for example corresponding to a first level of visual acuity, are presented to the user. During the evaluation step S18, the indications received by the user are evaluated and a score corresponding to the accuracy of the indications may be attributed to the user. If the user reaches a sufficient score, the displaying step S14, input receiving step S16 and evaluation step S18 may be repeated with a second series of various randomized optotypes, corresponding to a second level of visual acuity.

The disclosure further relates to a computer-readable storage medium having a program recorded thereon, wherein the program makes the computer execute a method according to the disclosure.

The disclosure also relates to a non-transitory program storage device, readable by a computer, tangibly embodying a program of instructions executable by the computer to perform the method according to the disclosure. For example, the method comprises the steps of measuring a distance d between a front camera of a mobile device and a mirror facing the front camera of the mobile device, displaying optotypes on a screen of the mobile device, receiving inputs from a user of the mobile device, and evaluating a visual acuity of the user based on the received inputs.

As illustrated on FIG. 4, the disclosure further relates to a mobile device 2 comprising at least a screen 4, at least one front camera 6, the screen and the front camera being placed on the same face of the mobile device, a memory 10 (not represented) configured to store sequences of instructions, and a processor 12 (not represented) coupled to the memory 10, the at least one screen 4 and the at least one front camera 6.

The processor 12 is configured to execute the sequences of instructions to measure a distance d between the front camera of a mobile device and a mirror facing the front camera of the mobile device, display optotypes on the screen of the mobile device, receive inputs from a user of the mobile device, and evaluate a visual acuity of the user based on the received inputs.

Figure 6:
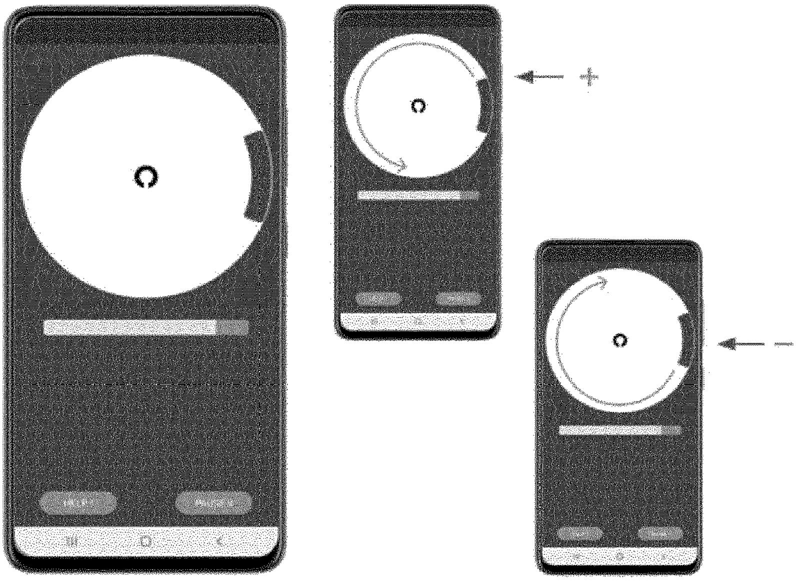
FIG. 6 illustrates a display system for use to determine the visual acuity of a person according to an embodiment of the disclosure.

As illustrated in FIG. 6, the disclosure further relates to a display system for use to determine the visual acuity of a person. For example, the display system is a system comprising a graphical user interface.

The display system comprises controlling means. The controlling means allow identifying and processing input data received from the user of the display system.

The display system further comprises displaying means. The displaying means allow displaying at least one optotype and at least one movable cursor. The at least one optotype is oriented in a direction selected from a list of predefined orientation. The movable cursor is configured to be positioned and displayed in any of the directions of the list of predefined directions. The position of the displayed movable cursor is determined based on the inputs received from the user, and identified and processed by the controlling means.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general-purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMS) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Many further modifications and variations will be apparent to those skilled in the art upon making reference to the foregoing illustrative embodiments, which are given by way of example only and which are not intended to limit the scope of the disclosure, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the disclosure.

The invention claimed is:

1. A method for evaluating a visual acuity of a person using a mobile device having at least a front camera and a screen, the method comprising:

positioning a user of a mobile device in front of a mirror at a predefined distance d/2, positioning the mobile device with the front camera of the mobile device facing the mirror;

measuring a distance d between the front camera of the mobile device and a virtual image of the mobile device in the mirror;

displaying optotypes on the screen of the mobile device;

receiving an indication from the user in response to the displayed optotype;

evaluating, using processing circuitry, the visual acuity of the user, based on the received indication from the user; and receiving mobile device data, the mobile device data including at least screen data relating at least to a physical size of the screen of the mobile device and camera data relating at least to an angular resolution of a front camera's pixel, wherein the distance d is measured based at least on the mobile device data, wherein the distance d/2 between the front camera and the mirror is regularly measured during the displaying and the evaluating, and wherein the size and/or angular size of the optotypes displayed during the displaying is adapted in real-time based on the measured distance d/2.

2. The method according to claim 1, further comprising, prior to the displaying, comparing the measured distance d to the predefined distance d/2.

3. The method according to claim 2, further comprising sending a notification to the user based on comparison of the measured distance d and the predefined distance d/2.

4. The method according to claim 1, wherein a size and/or angular size of the optotypes displayed during the displaying is adapted based on the measured distance d.

5. The method according to claim 1, wherein the optotypes displayed on the screen of the mobile device during the displaying includes a single Landolt-C with varying directions, and wherein the indication received from the user relates to a direction of an aperture of the Landolt-C perceived by the user.

6. The method according to claim 5, wherein the perceived direction of the Landolt-C aperture is indicated by the user using speech recognition and/or gesture recognition and/or movement of the mobile device.

7. The method according to claim 5, wherein the displayed optotype further includes a movable cursor and the perceived direction of the Landolt-C on the screen of the mobile device is indicated by a position of the movable cursor.

8. The method according to claim 7, wherein the mobile device includes physical plus and minus volume buttons, and wherein the movable cursor is controlled by the user using the physical plus and minus volume buttons of the mobile device.

9. The method according to claim 1, wherein the mobile device is holdable with a single hand.

* * * * *